(12) United States Patent
Busche et al.

(10) Patent No.: US 7,996,073 B2
(45) Date of Patent: Aug. 9, 2011

(54) SYSTEM AND METHOD FOR INTERPRETING ELECTROCARDIOGRAMS

(75) Inventors: Frederick D. Busche, Denton, TX (US); Bhooshan P. Kelkar, Flower Mound, TX (US)

(73) Assignee: International Business Machines Corporation, Armonk, NY (US)

( * ) Notice: Subject to any disclaimer, the term of this patent is extended or adjusted under 35 U.S.C. 154(b) by 924 days.

(21) Appl. No.: 10/963,968

(22) Filed: Oct. 13, 2004

(65) Prior Publication Data

US 2006/0079795 A1    Apr. 13, 2006

(51) Int. Cl.
    *A61B 5/04*    (2006.01)
(52) U.S. Cl. ........................... 600/513; 600/507
(58) Field of Classification Search .......... 600/509–510, 600/512–513, 516–519, 507, 9; 607/14, 607/28
    See application file for complete search history.

(56) References Cited

U.S. PATENT DOCUMENTS

| | | | |
|---|---|---|---|
| 3,880,147 A | | 4/1975 | Gruenke et al. |
| 5,184,615 A | * | 2/1993 | Nappholz et al. ............... 607/14 |
| 5,271,411 A | * | 12/1993 | Ripley et al. .................. 600/515 |
| 5,410,473 A | | 4/1995 | Kaneko et al. |
| 5,630,664 A | * | 5/1997 | Farrelly ........................ 600/508 |
| 5,749,367 A | * | 5/1998 | Gamlyn et al. ............... 600/509 |
| 5,819,007 A | * | 10/1998 | Elghazzawi .................... 706/46 |
| 5,956,013 A | | 9/1999 | Raj et al. |
| 6,238,350 B1 | | 5/2001 | Neilson |
| 6,434,417 B1 | * | 8/2002 | Lovett .......................... 600/509 |
| 6,438,410 B2 | * | 8/2002 | Hsu et al. ..................... 600/516 |
| 6,480,734 B1 | * | 11/2002 | Zhang et al. .................. 600/518 |
| 2001/0023419 A1 | | 9/2001 | LaPointe et al. |
| 2001/0049542 A1 | * | 12/2001 | Florio et al. ..................... 607/28 |
| 2003/0073914 A1 | | 4/2003 | Taha et al. |
| 2003/0171682 A1 | * | 9/2003 | Zhang et al. .................. 600/486 |
| 2004/0193064 A1 | * | 9/2004 | Shusterman .................. 600/504 |
| 2004/0243014 A1 | * | 12/2004 | Lee et al. ....................... 600/510 |

FOREIGN PATENT DOCUMENTS

| | | |
|---|---|---|
| DE | 19517138 A1 | 11/1996 |
| JP | 5184551 A | 7/1993 |
| JP | 6181898 A | 7/1994 |
| JP | 5176906 A | 4/1995 |
| JP | 10057331 A | 3/1998 |
| JP | 2002233513 A | 8/2002 |

* cited by examiner

*Primary Examiner* — Niketa I Patel
*Assistant Examiner* — Nicole F Lavert
(74) *Attorney, Agent, or Firm* — Andrea Bauer; Hoffman Warnick LLC

(57) ABSTRACT

A system and method for interpreting electrocardiogram data. A system is provided that clusters raw electrocardiogram (EKG) data into clusters of EKG data; generates a predictive model for each cluster of EKG data; compares inputted patient EKG data with the clusters of EKG data to identify a matching cluster of EKG data; applies the predictive model associated with the matching cluster of EKG data to the inputted patient EKG data; and outputs diagnostic data.

18 Claims, 2 Drawing Sheets

SYSTEM AND METHOD FOR INTERPRETING ELECTROCARDIOGRAMS

BACKGROUND OF THE INVENTION

1. Technical Field

The present invention relates generally to interpreting medical data, and more particularly relates to a system and method for interpreting electrocardiogram data.

2. Related Art

An electrocardiogram is an electrical recording of the heart and is used in the investigation of heart disease. Typically, the individual electrical measurement patterns are printed on a paper tape in a compressed format and the doctor, based upon his or her knowledge, interprets the result to ascertain whether irregularities in the working of the heart can be seen. The compression of the data and printing on paper does not allow for an analytical method to be used on the raw data to allow for quantification and comparison of that raw data except by the comparison by the doctor of the apparent pattern of measurements that are printed on the paper print out. A major benefit of using an electrocardiogram test is that it is a relatively quick and non-invasive procedure. Unfortunately, this approach is only about 65% effective in the determination of arterial blockage to the heart.

Accordingly, if the doctor is unsure of the proper diagnosis, the next step may be a CARDIOLITE® Technetium Tc99m Sestamibi test. (CARDIOLITE is a registered trademark of the E. I. Du Pont De Nemours and Company Corporation of Wilmington, Del.). CARDIOLITE is a tool for diagnosing coronary artery disease and identifying patients at risk for heart attacks and heart disease. The CARDIOLITE kit consists of a small protein named sestamibi that is marked with a radiopharmaceutical, technetium Tc99m sestamibi. It is injected into a patient intravenously and travels through the bloodstream to the heart. A patient undergoing a "rest-and-stress" exam receives two injections of CARDIOLITE, one while at rest and one while vigorously exercising on a stationary bike or treadmill. Pictures taken with a special camera during each of the two sessions allow doctors to visualize the radioactive tracer in the heart. Doctors then compare the pictures from the resting and stressful sessions to determine if the blood supply to the heart is being blocked. This is a costly procedure but not particularly invasive.

If the tools to perform a CARDIOLITE test are not available, a more invasive technique involving an angiogram may be selected. In an angiogram, a flexible catheter or tube is inserted into an artery, usually in the groin area, and guided through the arterial system into the heart and into the coronary arteries. A dye is then injected through the catheter into the bloodstream and x-rays of the heart and coronary arteries are taken. This technique is somewhat more dangerous than the CARDIOLITE test, but is usually quite diagnostic.

Unfortunately, both of the CARDIOLITE and angiogram tests have significant drawbacks, either in terms of costs or invasiveness. Instead, it would be preferable to rely on the results of the electrocardiogram test to make a more accurate diagnosis. Accordingly, a need exists for a more effective system for reading and/or analyzing the electrocardiogram test results using statistical and artificial intelligence algorithms as a means for this analysis.

SUMMARY OF THE INVENTION

The present invention addresses the above mentioned problems, as well as others, by providing a system, method and program product for interpreting electrocardiogram data.

Note that for the purposes of this disclosure, the terms electrocardiogram and ECG are generically referred to as an EKG. In a first aspect, the invention provides an EKG diagnosis system, comprising: a sequence analysis system for clustering raw EKG data into clusters of EKG data; and a predictive analysis system for generating a predictive model for each cluster of EKG data.

In a second aspect, the invention provides a program product stored on a recordable medium for interpreting electrocardiogram (EKG) data, comprising: means for clustering raw EKG data into clusters of EKG data; and means for generating a predictive model for each cluster of EKG data.

In a third aspect, the invention provides a method for interpreting electrocardiogram (EKG) data, comprising: clustering raw EKG data into clusters of EKG data; and generating a predictive model for each cluster of EKG data.

In a fourth aspect, the invention provides a method for deploying an application for interpreting electrocardiogram (EKG) data, comprising: providing a computer infrastructure being operable to: cluster raw EKG data into clusters of EKG data; generate a predictive model for each cluster of EKG data; compare inputted patient EKG data with the clusters of EKG data to identify a matching cluster of EKG data; apply the predictive model associated with the matching cluster of EKG data to the inputted patient EKG data; and output diagnostic data.

In a fifth aspect, the invention provides computer software embodied in a propagated signal for interpreting electrocardiogram data, the computer software comprising instructions to cause a configuration computer to perform the following functions: cluster raw EKG data into clusters of EKG data; generate a predictive model for each cluster of EKG data; compare inputted patient EKG data with the clusters of EKG data to identify a matching cluster of EKG data; apply the predictive model associated with the matching cluster of EKG data to the inputted patient EKG data; and output diagnostic data.

BRIEF DESCRIPTION OF THE DRAWINGS

These and other features of this invention will be more readily understood from the following detailed description of the various aspects of the invention taken in conjunction with the accompanying drawings in which.

DETAILED DESCRIPTION OF THE INVENTION

Figure 1:
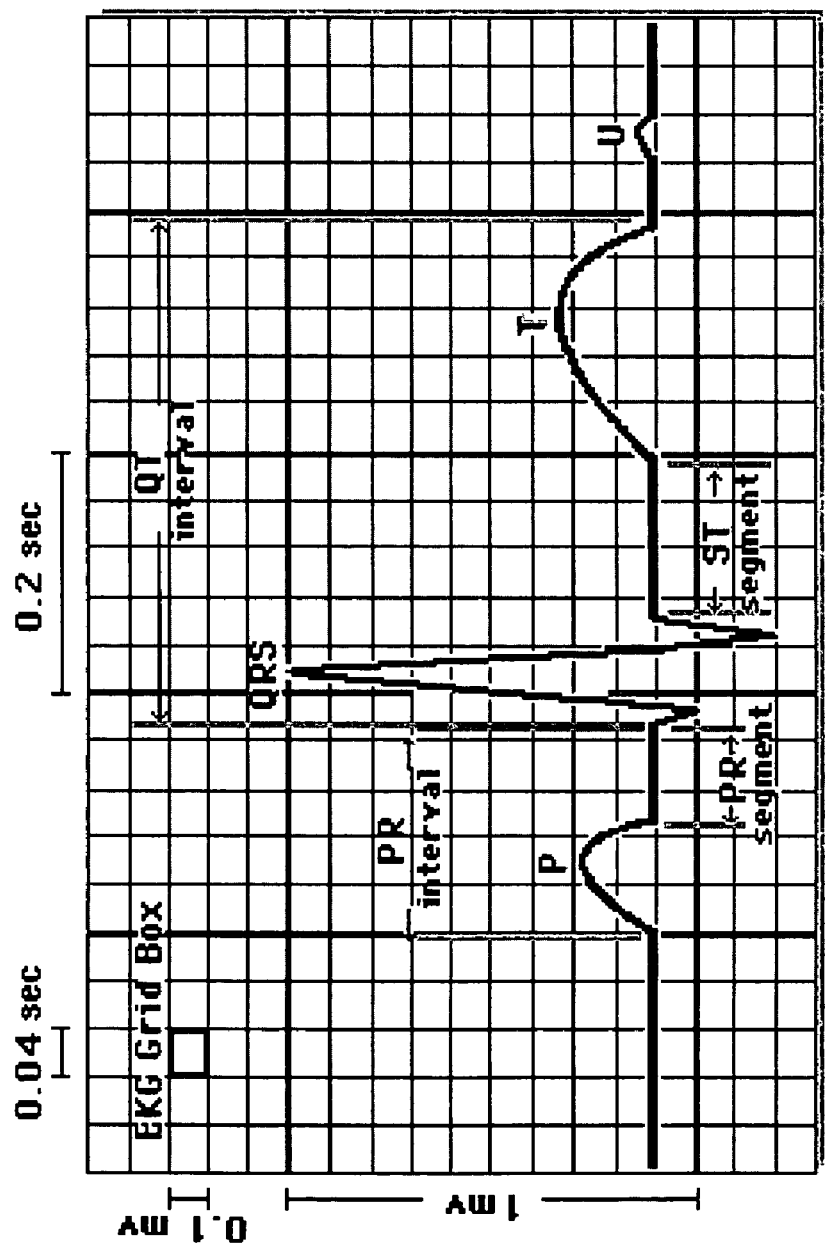
FIG. 1 depicts an EKG data pattern, in accordance with the present invention.

As shown in FIG. 1, EKG patterns have a fairly uniform signature, which when broken into various components, can be interpreted to evaluate the patient. As can be seen, these components include a PR interval, a PR segment, an ST segment, a QT interval, and P, QRS, T and U waves. The present invention analytically evaluates the signature of an inputted pattern relative to a database of existing EKG patterns. Predictive analysis is utilized provide a probability that a selected diagnosis is correct for the patient.

Figure 2:
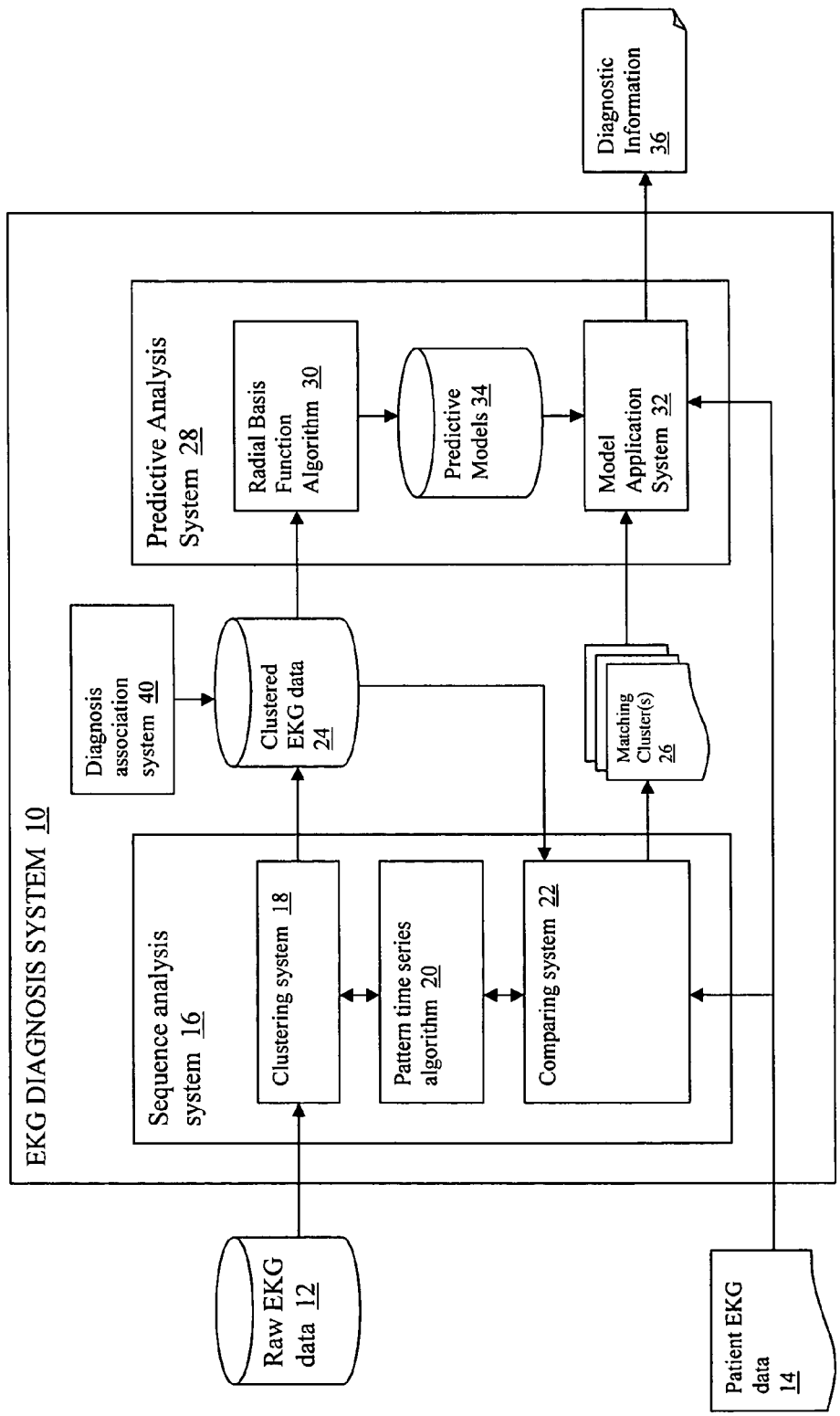
FIG. 2 depicts an EKG diagnosis system in accordance with the present invention.

FIG. 2 depicts an illustrative EKG diagnosis system 10 in which diagnostic information 36 is generated in response to inputted patient EKG data 14. As will be described in more detail below, EKG diagnosis system 10 includes a sequence analysis system 16 and a predictive analysis system 28, which facilitate the diagnostic process.

In order to effectuate the process, raw EKG data 12 is first collected, clustered and modeled. Raw EKG data 12 may comprise, e.g., digitized EKG pattern data captured from various subjects over time. In addition to raw EKG data 12, EKG diagnosis system 10 maintains a database of clustered EKG data 24 and a database of predictive models 34 (e.g., one model for each cluster). Information in these databases may be static or dynamic, i.e., they may be regularly updated with new data to create a larger knowledge base and more accurate results.

Clustering of the raw EKG data 12 is performed by clustering system 18. Clustering system 18 utilizes a pattern time series algorithm 20 to identify and cluster sets of EKG patterns that have similar pattern signatures. Pattern time series algorithm 20 examines the data points from different EKG patterns to identify similar overall patterns. Such algorithms are commonly used in applications such as identifying pairs of similar images, retrieving music scores, discovering stocks with similar performance characteristics, etc.

A simplified example in the current context is described with reference to the data shown in Table 1. As can be seen, Table 1 includes seven EKG time sequences, EKG1-EKG7, with each sequence having six time samples.

TABLE 1

| EKG | t = 1 | t = 2 | t = 3 | t = 4 | t = 5 | t = 6 |
|---|---|---|---|---|---|---|
| EKG1 | 0.1 | 0.2 | 0.3 | 0.4 | 0.5 | 0.6 |
| EKG2 | 1 | 2 | 3 | 4 | 5 | 6 |
| EKG3 | 1 | 1 | 10 | 1 | 1 | 1 |
| EKG4 | 2 | 2 | 2 | 2 | 2 | 2 |
| EKG5 | 1 | 0.8 | 0.6 | 0.4 | 0.2 | 0 |
| EKG6 | 10 | 10 | 6 | 4 | 2 | 0 |
| EKG7 | 0 | 0.4 | 0.6 | 0.8 | 1 | 1.2 |

Various approaches using a pattern time series algorithm 20 may be employed to cluster similar EKG data sets. In a simple embodiment, the algorithm might simply look for sequences that have the same values at corresponding times, or similar values within some threshold. In more complex analysis, other criteria for identifying similarity amongst patterns may be utilized. For example, using a "scale invariant" analysis, patterns that share the same trends, but are of a different scale, may be identified as similar. For instance, it can be seen that even though EKG1 and EKG2 are in different scale, the underlying trend is the same, and thus the pattern time series algorithm 20 may conclude that the two patterns are similar. Moreover, using a "subsequence matching" analysis, the pattern time series algorithm 20 could conclude that EKG1 and EKG7 are similar even though the slope of EKG7 is steeper. In particular, it can be seen that for the times t=3 to t=6, EKG1 and EKG7 have the same pattern. Because they have matching subsequences, the two patterns might be identified as similar. Furthermore, using a "shift in time" analysis, the algorithm 20 could cluster patterns that are time shifted relative to one another, but are otherwise similar.

Pattern time series algorithm 20 could also consider noise when identifying similar patterns. For example, EKG3 and EKG4 are similar except for the value 10 at t=3 of EKG3. This value could be discounted as an outlier, introduced either due to manual or instrumental error. In this case, the algorithm would considered only the subsequences t=1 to t=2, and t=4 to t=6.

Using these approaches for the above example shown in table 1, an output table could be generated as shown in table 2. Table 2 lists different EKG pattern pairs EKG A, EKG B; a match fraction, and the number of subsequences. The match fraction, for instance, may indicate the fractional number of time values that are similar (i.e., share the same value within some threshold) for two patterns.

TABLE 2

| EKG A | EKG B | Match | subsequences |
|---|---|---|---|
| EKG1 | EKG2 | 1 | 1 |
| EKG1 | EKG7 | 0.6 | 1 |
| EKG2 | EKG7 | 0.6 | 1 |
| EKG3 | EKG4 | 0.8 | 2 |
| EKG5 | EKG6 | 0.7 | 1 |
| EKG3 | EKG6 | 0.2 | 1 |
| EKG4 | EKG6 | 0.2 | 1 |
| . | . | . | . |
| . | . | . | . |
| . | . | . | . |

In an illustrative embodiment, EKG pairs having a match fraction higher than a predetermined threshold (e.g., >0.5) can be clustered together. Using associative logic, result could be combined, e.g., if A is similar to B, and B is similar to C, then ABC are similar. In this case, there would be three clusters:

Cluster 1: EKG1, EKG2, EKG7
Cluster 2: EKG3, EKG4
Cluster 3: EKG5, EKG6

Because all other match fractions are less than 0.5, they would not be included in the cluster building logic. Each cluster can then be associated with a particular "condition" or diagnosis by diagnosis association system 40. For example, Cluster 1 may be indicative of a healthy pattern, Cluster 2 may be indicative of a first predefined condition, and Cluster 3 may be indicative of a second predefined condition. Any mechanism for associating clusters to diagnoses could be utilized.

After the database of clustered EKG data 24 is generated, predictive analysis system 28 can generate a predictive model for each cluster. To accomplish this, a radial basis function (RBF) algorithm 30 can be utilized. The purpose of predicting values is to discover the dependency and the variation of one field's value upon the values of the other fields within the same record. A model is generated that can predict a value for that particular field in a new record of the same form, based on other field values.

For example, consider a retailer who wants to use historical data to estimate the sales revenue for a new customer. A mining run on this historical data creates a model. This model can be used to predict the expected sales revenue for a new customer, based on the new customer's data. The model might also show that for some customers, incentive campaigns improve sales. In addition, it might reveal that frequent visits by sales representatives lead to a lower revenue if the customer is young.

On a practical level, the algorithms process a table of data in which every record has an identical format. A single field within the table must be designated as containing the value to be fitted, while the coordinates are selected from the other fields in the table. One can use a Radial-Basis Function (RBF) method to fit data that is a function of many variables. The basic algorithm can form a model that predicts the value of a particular field from the other attribute values.

A Radial-Basis Function fitting requires a number of fitting centers. A fitting center is a vector in the attribute space. At each of these centers, a basis function is defined. The basis function is a nonlinear function of distance from the fitting center. This is why the basis functions are called Radial-Basis Functions; they have the same value for any point with the same distance or radius from the fitting center.

The prediction given by the radial-basis fit for a particular set of attributes (called a point) is a weighted sum of these basis functions at that point. During the fitting process, the weight values producing the best fits are determined at each fitting center. In addition, it is decided where the fitting centers are placed.

RBFs divide the data space into small regions, and build separate models for each region. Separate regions of data space, which may have few functional relationships among them, are given separate models. Radial basis functions are the natural generalization of coarse coding to continuous-valued features. Rather than each feature being either 0 or 1, it can be anything in the interval [0, 1], reflecting various degrees to which the feature is present. A typical RBF feature, i, has a gaussian (bell-shaped) response, $\phi_s(i)$, dependent only on the distance between the state, s, and the feature's proto-typical or center state, $c_i$, and relative to the feature's width, $\sigma_i$:

$$\phi_s(i) = \exp\left(-\frac{\|s - c_i\|^2}{2\sigma_i^2}\right).$$

The norm or distance metric of course can be chosen in whatever way seems most appropriate to the states and task at hand. An advantage of RBFs over binary features is that they produce approximate functions that vary smoothly and are differentiable. Such nonlinear methods may be able to fit the target function much more precisely.

The result of RBF algorithm 30, when applied to the cluster data, is a probability model that can be associated with each cluster. In other words, each predictive model provides a likelihood or probability that the patterns in a given cluster are representative of a common "condition" or diagnosis as established diagnosis association system 40.

Once the clustered EKG data 24 and predictive models 34 are generated, EKG diagnosis system 10 can be utilized to evaluate patient EKG data 14 and generate diagnostic data 36. In a typical embodiment, patient EKG data 14 is collected and inputted in a digital format. Initially, sequence analysis system 16 utilizes a comparing system 22, which compares the inputted EKG data 14 with the clustered EKG data 24 to identify one or more matching cluster(s) 26. Comparing system 22 may utilize the pattern time series algorithm 20, in a similar manner to that described above.

Once the matching cluster(s) 26 are identified, model application system 32 can apply the predictive models 34 associated with the matching cluster(s) 26 to the inputted patient EKG data 14. The result is diagnostic data 36, which may for example list one or more diagnoses and an associated probability for each diagnosis.

The approach discussed above will allow the doctor to be more accurate in his analysis of EKG results and therefore reduce the need for tests that are either more invasive, expensive or both. This approach will lower hospital diagnostic costs to health care providers and patients and may even produce lower levels of mortality associated with the evaluation of heart disease.

It should be appreciated that EKG diagnosis system 10 of the present invention could be carried out on a stand-alone computer system, or over a network such as the Internet, a local area network (LAN), a wide area network (WAN), a virtual private network (VPN), etc. Suitable computer systems may include a mainframe, a desktop computer, a laptop computer, a workstation, a hand held device, a client, a server, etc. In any event, the computer system may generally comprise, e.g., a processing unit, memory, a bus, input/output (I/O) interfaces, external devices/resources and a storage unit. The processing unit may comprise a single processing unit, or processors distributed across one or more processing units in one or more locations, e.g., on a client and server. Memory may comprise any known type of data storage and/or transmission media, including magnetic media, optical media, random access memory (RAM), read-only memory (ROM), a data cache, a data object, etc. Moreover, similar to processing unit, memory may reside at a single physical location, comprising one or more types of data storage, or be distributed across a plurality of physical systems in various forms.

I/O interfaces may comprise any system for exchanging information to/from an external source. External devices/resources may comprise any known type of external device, including a scanner, a storage device, a network connection, speakers, a hand-held device, a keyboard, a mouse, a voice recognition system, a speech output system, a printer, a monitor/display, a facsimile, a pager, etc.

Databases 12, 24, 34 may each comprise any type of storage unit capable of providing storage for information under the present invention. As such, the storage units could include one or more storage devices, such as a magnetic disk drive or an optical disk drive. Moreover, the storage units may include data distributed across, for example, a local area network (LAN), wide area network (WAN) or a storage area network (SAN).

Thus, it should also be understood that while the invention is described as a single integrated architecture, the invention could be implemented in a distributed fashion where the components and subsystems do not necessarily reside at the same physical location.

It should also be understood that the present invention can be realized in hardware, software, a propagated signal, or any combination thereof. Any kind of computer/server system(s)- or other apparatus adapted for carrying out the methods described herein—is suited. A typical combination of hardware and software could be a general purpose computer system with a computer program that, when loaded and executed, carries out the respective methods described herein. Alternatively, a specific use computer, containing specialized hardware for carrying out one or more of the functional tasks of the invention, could be utilized. The present invention can also be embedded in a computer program product or a propagated signal, which comprises all the respective features enabling the implementation of the methods described herein, and which—when loaded in a computer system—is able to carry out these methods. Computer program, propagated signal, software program, program, or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

It should also be appreciated that the teachings of the present invention can be offered as a business method on a subscription or fee basis. For example, a computer system could be created, maintained, supported, and/or deployed by a service provider that offers the functions described herein for customers.

The foregoing description of the preferred embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

The invention claimed is:

1. A computer-implemented electrocardiogram (EKG) diagnosis system, comprising:
   a sequence analysis system for identifying EKG data patterns in raw EKG data and clustering the EKG data patterns into clusters of EKG data patterns,
      wherein the EKG data patterns include a PR interval, a PR segment, an ST segment, a QT interval, and P, QRS, T, and U waves,
      wherein each of the clusters comprises a plurality of EKG data patterns, and wherein each of the EKG data patterns within a cluster shares a similar pattern signature, and has a dissimilar pattern signature from EKG data patterns outside the cluster;
   a predictive analysis system for generating a predictive model for each cluster of EKG data patterns;
   a system for associating a diagnosis with each cluster, wherein the diagnosis is one of a healthy condition or one of at least one predefined health condition,
   wherein the predictive model provides a probability determined based on a radial basis function that the pattern signature of each of the plurality of clusters is representative of the diagnosis; and
   a system for outputting diagnostic data for each cluster of EKG data patterns, wherein the diagnostic data includes the probability that the pattern signature of each of the plurality of clusters is representative of the diagnosis.

2. The EKG diagnosis system of claim 1, wherein the sequence analysis system includes a pattern time series algorithm for evaluating similarities among clusters of EKG data patterns and identifying and clustering EKG patterns having similar data patterns.

3. The EKG diagnosis system of claim 1, wherein the sequence analysis system includes a comparing system for comparing inputted patient EKG data patterns with the clusters of EKG data patterns to identify a matching cluster of EKG data patterns.

4. The EKG diagnosis system of claim 3, wherein the predictive analysis system includes a system for applying the predictive model associated with the matching cluster of EKG data patterns to the inputted patient EKG data pattern, and for outputting diagnostic data.

5. The EKG diagnosis system of claim 4, wherein diagnostic data includes a diagnosis and a probability associated with the diagnosis.

6. The EKG diagnosis system of claim 2, wherein the pattern time series algorithm comprises one of:
   an algorithm that identifies sequences having a same value or a similar value within a threshold at a corresponding time,
   an algorithm that uses a scale invariant analysis to identify sequences that share a similar trend but are of a different scale,
   an algorithm that uses a subsequence matching analysis to identify sequences that are similar despite differences in slope, and
   an algorithm that uses a shift in time analysis to identify sequences that are time shifted relative to one another, but are otherwise similar.

7. A program product stored on a recordable non-transitory storage medium for interpreting electrocardiogram (EKG) data comprising: means for identifying EKG patterns in raw EKG data and clustering the EKG data patterns into clusters of EKG patterns, wherein the EKG patterns include a PR interval, a PR segment, an ST segment, a QT interval, and P, QRS, T, and U waves, wherein each of the clusters comprises a plurality of EKG patterns, and wherein each of the EKG data patterns within a cluster shares a similar pattern signature, and has a dissimilar pattern signature from EKG data patterns outside the cluster; means for generating a predictive model for each cluster of EKG data patters; means for associating a diagnosis with each cluster, wherein the diagnosis with each cluster, wherein the diagnosis is one of a healthy condition or one of at least one predefined health condition, wherein the predictive model provides a probability determined based on a radial basis function that the pattern signature of each of the plurality of clusters is representative of the diagnosis; and means for outputting diagnostic data for each cluster of EKG data patterns, wherein the diagnostic data includes the probability that the pattern signature of each of the plurality of clusters is representative of the diagnosis.

8. The program product of claim 7, wherein the clustering means includes a pattern time series algorithm for evaluating similarities among clusters of EKG data patterns and identifying and clustering EKG patterns having similar data patterns.

9. The program product of claim 7, further comprising means for comparing inputted patient EKG data patterns with the clusters of EKG data patterns to identify a matching cluster of EKG data patterns.

10. The program product of claim 9, further comprising means for applying the predictive model associated with the matching cluster of EKG data patterns to the inputted patient EKG data patterns, and for outputting diagnostic data.

11. The program product of claim 10, wherein diagnostic data includes a diagnosis and a probability associated with the diagnosis.

12. The program product of claim 8, wherein the pattern time series algorithm comprises one of:
   an algorithm that identifies sequences having a same value or a similar value within a threshold at a corresponding time,
   an algorithm that uses a scale invariant analysis to identify sequences that share a similar trend but are of a different scale,
   an algorithm that uses a subsequence matching analysis to identify sequences that are similar despite differences in slope, and
   an algorithm that uses a shift in time analysis to identify sequences that are time shifted relative to one another, but are otherwise similar.

13. A method for interpreting electrocardiogram (EKG) data, comprising:
   identifying EKG data patterns in raw EKG data and clustering the EKG data patterns into clusters of EKG data patterns,
      wherein the EKG data patterns include a PR interval, a PR segment, an ST segment, a QT interval, and P, QRS, T, and U waves,
      wherein each of the clusters comprises a plurality of EKG data patterns, and wherein each of the EKG data patterns within a cluster shares a similar pattern signature, and has a dissimilar pattern signature from EKG data patterns outside the cluster;
   generating a predictive model for each cluster of EKG data patterns; and
   associating a diagnosis with each cluster, wherein the diagnosis is one of a healthy condition or one of at least one predefined health condition, and wherein the predictive model provides a probability determined based on a radial basis function that the pattern signature of each of the plurality of clusters is representative of the diagnosis, and outputting diagnostic data for each cluster of EKG data patterns, wherein the diagnostic data includes the probability that the pattern signature of each of the plurality of clusters is representative of the diagnosis.

14. The method of claim 13, wherein the clustering step utilizes a pattern time series algorithm for evaluating similarities among clusters of EKG data patterns and identifying and clustering EKG patterns having similar data patterns.

15. The method of claim 13, further comprising the steps of:

comparing inputted patient EKG data patterns with the clusters of EKG data patterns to identify a matching cluster of EKG data patterns; and applying the predictive model associated with the matching cluster of EKG data patterns to the inputted patient EKG data patterns.

16. The method of claim 14, wherein the pattern time series algorithm comprises one of:

an algorithm that identifies sequences having a same value or a similar value within a threshold at a corresponding time, an algorithm that uses a scale invariant analysis to identify sequences that share a similar trend but are of a different scale, an algorithm that uses a subsequence matching analysis to identify sequences that are similar despite differences in slope, and an algorithm that uses a shift in time analysis to identify sequences that are time shifted relative to one another, but are otherwise similar.

17. A method for deploying an application for interpreting electrocardiogram (EKG) data, comprising:

providing a computer infrastructure being operable to:

identify EKG data patterns in raw EKG data and cluster the EKG data patterns into clusters of EKG data patterns, wherein the EKG data patterns include a PR interval, a PR segment, an ST segment, a QT interval, and P, QRS, T, and U waves, wherein each of the clusters comprises a plurality of EKG data patterns, and wherein each of the EKG data patterns within a cluster shares a similar pattern signature, and has a dissimilar pattern signature from EKG data patterns outside the cluster;

generate a predictive model for each cluster of EKG data patterns;

compare inputted patient EKG data patterns with the clusters of EKG data patterns to identify a matching cluster of EKG data patterns;

associate a diagnosis with each cluster, wherein the diagnosis is one of a healthy condition or one of at least one predefined health condition;

apply the predictive model associated with the matching cluster of EKG data patterns to the inputted patient EKG data patterns, wherein the predictive model provides a probability determined based on a radial basis function that the pattern signature of each of the plurality of clusters is representative of the diagnosis; and output diagnostic data for each cluster of EKG data patterns, wherein the diagnostic data includes the probability that the pattern signature of each of the plurality of clusters is representative of the diagnosis.

18. A method of interpreting electrocardiogram data, the method comprising:

identifying EKG data patterns in raw EKG data and clustering the EKG data patterns into clusters of EKG data patterns, wherein the EKG data patterns include a PR interval, a PR segment, an ST segment, a QT interval, and P, QRS, T, and U waves, wherein each of the clusters comprises a plurality of EKG data patterns, and wherein each of the EKG data patterns within a cluster shares a similar pattern signature, and has a dissimilar pattern signature from EKG data patterns outside the cluster;

generating a predictive model for each cluster of EKG data patterns;

comparing inputted patient EKG data patterns with the clusters of EKG data patterns to identify a matching cluster of EKG data patterns;

associating a diagnosis with each cluster, wherein the diagnosis is one of a healthy condition or one of at least one predefined health condition;

applying the predictive model associated with the matching cluster of EKG data patterns to the inputted patient EKG data patterns, wherein the predictive model provides a probability determined based on a radial basis function that the pattern signature of each of the plurality of clusters is representative of the diagnosis; and outputting diagnostic data for each cluster of EKG data patterns, wherein the diagnostic data includes the probability that the pattern signature of each of the plurality of clusters is representative of the diagnosis.

* * * * *